United States Patent
Bammel et al.

(10) Patent No.: US 7,030,263 B2
(45) Date of Patent: *Apr. 18, 2006

(54) METHOD OF PREPARING A CARBAMATE- OR UREA-FUNCTIONAL COMPOUND

(75) Inventors: Brian D. Bammel, Rochester Hills, MI (US); John D. McGee, Troy, MI (US); Walter H. Ohrbom, Hartland Township, MI (US); Todd A. Seaver, Fort Wayne, IN (US); Gregory G. Menovcik, Farmington Hills, MI (US); Paul J. Harris, West Bloomfield, MI (US); John W. Rehfuss, Huntersville, NC (US)

(73) Assignee: BASF Corporation, Southfield, MI (US)

( * ) Notice: Subject to any disclaimer, the term of this patent is extended or adjusted under 35 U.S.C. 154(b) by 339 days.

This patent is subject to a terminal disclaimer.

(21) Appl. No.: 10/280,619

(22) Filed: Oct. 25, 2002

(65) Prior Publication Data

US 2003/0050498 A1    Mar. 13, 2003

Related U.S. Application Data

(62) Division of application No. 08/698,525, filed on Aug. 15, 1996, now Pat. No. 6,498,266.

(51) Int. Cl.
*C08G 63/64* (2006.01)

(52) U.S. Cl. ............... 560/24; 428/423.1; 525/410; 525/414; 525/415; 525/450; 525/509; 525/519

(58) Field of Classification Search ............... 560/24; 428/423.1; 525/410, 414, 415, 450, 509, 525/519

See application file for complete search history.

(56) References Cited

U.S. PATENT DOCUMENTS

| | | | | |
|---|---|---|---|---|
| 5,760,127 A | * | 6/1998 | Bammel et al. | 524/590 |
| 5,770,650 A | * | 6/1998 | McGee et al. | 524/590 |
| 5,792,810 A | * | 8/1998 | Menovcik et al. | 524/590 |
| 5,827,930 A | * | 10/1998 | Ohrbom et al. | 525/440 |
| 5,854,385 A | * | 12/1998 | McGee et al. | 528/369 |
| 6,084,038 A | * | 7/2000 | Ohrbom et al. | 525/481 |
| 6,291,073 B1 | * | 9/2001 | Ohrbom et al. | 428/423.1 |
| 6,624,241 B1 | * | 9/2003 | Weise et al. | 524/591 |

* cited by examiner

*Primary Examiner*—Peter O'Sullivan

(57) ABSTRACT

A method of preparing a carbamate or urea-functional compound is described comprising the step of reacting a lactone or hydroxy carboxylic acid with a compound (A) comprising a carbamate or urea group or a group that can be converted to a carbamate or urea group, and an active hydrogen group capable of reacting with the hydroxy carboxylic acid or in a ring-opening reaction with a lactone. The compound thus prepared is useful in curable compositions.

4 Claims, No Drawings

METHOD OF PREPARING A CARBAMATE- OR UREA-FUNCTIONAL COMPOUND

This application is a divisional application of Ser. No. 08/698,525, filed on Aug. 15, 1996, now U.S. Pat. No. 6,498,266.

FIELD OF THE INVENTION

This invention relates to methods of preparing compounds, particularly carbamate- or urea-functional compounds, particularly compounds useful in curable compositions such as coating compositions.

BACKGROUND OF THE INVENTION

Carbamate- or urea-functional compositions have been described for uses such as curable compositions, particularly curable coating compositions. They are often used for topcoats in the automotive and industrial coatings industry. Color-plus-clear composite coatings are particularly useful as topcoats where exceptional gloss, depth of color, distinctness of image, or special metallic effects are desired. The automotive industry has made extensive use of these coatings for automotive body panels. Color-plus-clear composite coatings, however, require an extremely high degree of clarity in the clearcoat to achieve the desired visual effect. High-gloss coatings also require a low degree of visual aberations at the surface of the coating in order to achieve the desired visual effect such as high distinctness of image (DOI).

Such coatings are especially susceptible to a phenomenon known as environmental etch. Environmental etch manifests itself as spots or marks on or in the finish of the coating that often cannot be rubbed out.

Curable coating compositions based on curable components having carbamate or urea functionality have been proposed have been described in the art to provide etch-resistant coatings, e.g., U.S. Pat. No. 5,356,669 and WO 94/10211.

In addition to resistance to environmental etch, a number of other characteristics can be desirable. For example, it may be desireable to provide a coating having a high degree of flexibility. This can be particularly advantageous if the substrate on which the coating is placed is itself flexible, as in the case of plastic, leather, or textile substrates.

It is also desirable to reduce the amount of solvent required in coating compositions in order to reduce the volatile organic content (VOC), which is better for the environment.

Finally, it is desirable to provide options of different types of carbamate- or urea-functional materials to provide coatings with a good combination of properties such as durability, hardness, and resistance to scratching, marring, solvents, and acids.

SUMMARY OF THE INVENTION

According to the present invention, there is provided a method of preparing carbamate- or urea-functional compounds capable of providing one or more of the above-described properties. This method comprises a method of making a carbamate- or urea-functional ester-containing compound comprising the step of reacting a lactone or hydroxy carboxylic acid with a compound (A) comprising a carbamate or urea group or a group that can be converted to a carbamate or urea group, and an active hydrogen group capable of reacting with the hydroxy carboxylic acid or in a ring-opening reaction with a lactone.

Compounds prepared according to the present invention can provide coatings having a good combination of properties such as durability, hardness, and resistance to scratching, marring, solvents, and acids. Such coating compositions can also provide low VOC levels, and can be used to prepare coatings having good flexibility for use over flexible substrates.

DESCRIPTION OF THE PREFERRED EMBODIMENTS

According to the present invention, a compound having carbamate or urea functionality is formed by reaction of a compound (A) having carbamate or urea groups or groups that can be converted to carbamate or urea, and an active hydrogen group.

Carbamate groups can generally be characterized by the formula

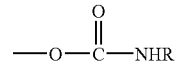

wherein R is H or alkyl, preferably of 1 to 4 carbon atoms. Preferably, R is H or methyl, and more preferably R is H. Urea groups can generally be characterized by the formula

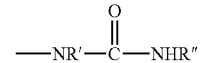

wherein R' and R" each independently represents H or alkyl, preferably of 1 to 4 carbon atoms, or R' and R" may together form a heterocyclic ring structure (e.g., where R' and R" form an ethylene bridge).

According to the present invention, the carbamate- or urea-functional compound can be formed by reacting a lactone or hydroxy carboxylic acid with a compound (A) having an active hydrogen group capable of ring-opening the lactone or undergoing a condensation reaction with the hydroxy carboxylic acid (e.g., hydroxyl, primary amine, acid) and a carbamate or urea group or a group that can be converted to carbamate or urea. When a compound having an active hydrogen group and a group that can be converted to carbamate or urea is used to ring-open the lactone or react with the hydroxy carboxylic acid, conversion of the group to a carbamate or urea can be accomplished during or after the ring-opening reaction.

Compounds having a carbamate or urea group and an active hydrogen group are known in the art. Hydroxypropyl carbamate and hydroxyethyl ethylene urea, for example, are well known and commercially available. Amino carbamates are described in U.S. Pat. No. 2,842,523. Hydroxyl ureas may also be prepared by reacting an oxazolidone with ammonia or a primary amine or by reacting ethylene oxide with ammonia to form an amino alcohol and then reacting the amine group of that compound or any other amino alcohol with hydrochloric acid, then urea to form a hydroxy urea. Amino ureas can be prepared, for example, by reacting a ketone with a diamine having one amine group protected from reaction (e.g., by steric hindrance), followed by reaction with HNCO (i.e., the product of the thermal decomposition of urea), and then water. Alternatively, these compounds can be prepared by starting with a compound having an active hydrogen and a group that can be converted to carbamate or urea as described below, and then converting that group to the carbamate or urea prior to commencement of the reaction with the lactone or hydroxy carboxylic acid.

Groups that can be converted to carbamate include cyclic carbonate groups, epoxy groups, and unsaturated bonds. Cyclic carbonate groups can be converted to carbamate groups by reaction with ammonia or a primary amine, which ring-opens the cyclic carbonate to form a β-hydroxy carbamate. Epoxy groups can be converted to carbamate groups by first converting to a cyclic carbonate group by reaction with $CO_2$. This can be done at any pressure from atmospheric up to supercritical $CO_2$ pressures, but is preferably under elevated pressure (e.g., 60–150 psi). The temperature for this reaction is preferably 60–150° C. Useful catalysts include any that activate an oxirane ring, such as tertiary amine or quaternary salts (e.g., tetramethyl ammonium bromide), combinations of complex organotin halides and alkyl phosphonium halides (e.g., $(CH_3)_3SnI$, $Bu_4SnI$, $Bu_4PI$, and $(CH_3)_4PI$), potassium salts (e.g., $K_2CO_3$, KI) preferably in combination with crown ethers, tin octoate, calcium octoate, and the like. The cyclic carbonate group can then be converted to a carbamate group as described above. Any unsaturated bond can be converted to carbamate groups by first reacting with peroxide to convert to an epoxy group, then with $CO_2$ to form a cyclic carbonate, and then with ammonia or a primary amine to form the carbamate.

Other groups, such as hydroxyl groups or isocyanate groups can also be converted to carbamate groups to form a compound (A). However, if such groups were to be present on the compound (A) and then converted to carbamate after reaction with the lactone or hydroxy carboxylic acid, they would have to be blocked so that they would not react with the lactone or hydroxy carboxylic acid or with active hydrogen groups that are present. When blocking these groups is not feasible, the conversion to carbamate or urea would have to be completed prior to the reaction with the lactone or hydroxy carboxylic acid. Hydroxyl groups can be converted to carbamate groups by reaction with a monoisocyanate (e.g., methyl isocyanate) to form a secondary carbamate group or with cyanic acid (which may be formed in situ by thermal decomposition of urea) to form a primary carbamate group (i.e., unsubstituted carbamates). This reaction preferably occurs in the presence of a catalyst as is known in the art. A hydroxyl group can also be reacted with phosgene and then ammonia to form a compound having primary carbamate group(s), or by reaction of a hydroxyl with phosgene and then a primary amine to form a compound having secondary carbamate groups. Another approach is to react an isocyanate with a compound such as hydroxyalkyl carbamate to form a carbamate-capped isocyanate derivative. For example, one isocyanate group on toluene diisocyanate can be reacted with hydroxypropyl carbamate, followed by reaction of the other isocyanate group with an excess of polyol to form a hydroxy carbamate. Finally, carbamates can be prepared by a transesterification approach where hydroxyl group reacted with an alkyl carbamate (e.g., methyl carbamate, ethyl carbamate, butyl carbamate) to form a primary carbamate group-containing compound. This reaction is performed under heat, preferably in the presence of a catalyst such as an organometallic catalyst (e.g., dibutyltin dilaurate). Other techniques for preparing carbamates are also known in the art and are described, for example, in P. Adams & F. Baron, "Esters of Carbamic Acid", *Chemical Review*, v. 65, 1965.

Groups such as oxazolidone can also be converted to urea after reaction with the lactone or hydroxy carboxylic acid. For example, hydroxyethyl oxazolidone can be used to initiate the reaction with the lactone or hydroxy carboxylic acid, followed by reaction of ammonia or a primary amine with the oxazolidone to generate the urea functional group.

Other groups, such as amino groups or isocyanate groups can also be converted to urea groups to form a compound (A). However, if such groups were to be present on the compound (A) and then converted to urea after reaction with the lactone or hydroxy carboxylic acid, they would have to be blocked so that they would not react with the lactone, the hydroxy carboxylic acid, or with the active hydrogen groups. When blocking these groups is not feasible, the conversion to carbamate or urea would have to be completed prior to reaction with the lactone or hydroxy carboxylic acid. Amino groups can be converted to urea groups by reaction with a monoisocyanate (e.g., methyl isocyanate) to form a secondary urea group or with cyanic acid (which may be formed in situ by thermal decomposition of urea) to form a primary urea group. This reaction preferably occurs in the presence of a catalyst as is known in the art. An amino group can also be reacted with phosgene and then ammonia to form a compound having primary urea group(s), or by reaction of an amino group with phosgene and then a primary amine to form a compound having secondary urea groups. Another approach is to react an isocyanate with a hydroxy urea compound to form a urea-capped isocyanate derivative. For example, one isocyanate group on toluene diisocyanate can be reacted with hydroxyethyl ethylene urea, followed by reaction of the other isocyanate group with an excess of polyol to form a hydroxy carbamate.

One preferred class of compounds having an active hydrogen group and a group that can be converted to carbamate is the hydroxyalkyl cyclic carbonates. Hydroxyalkyl cyclic carbonates can be prepared by a number of approaches. Certain hydroxyalkyl cyclic carbonates like 3-hydroxypropyl carbonate (i.e., glycerine carbonate) are commercially available. Cyclic carbonate compounds can be synthesized by any of several different approaches. One approach involves reacting an epoxy group-containing compound with $CO_2$, under conditions and with catalysts as described hereinabove. Useful catalysts include any that activate an oxirane ring, such as tertiary amine quaternary salts (e.g., tetramethyl ammonium bromide), tin and/or phosphorus complex salts (e.g., $(CH_3)_3SnI$, $(CH_3)_4PI$). Epoxides can also be reacted with β-butyrolactone in the presence of such catalysts. In another approach, a glycol like glycerine is reacted at temperatures of at least 80° C. with diethyl carbonate in the presence of a catalyst (e.g., potassium carbonate) to form a hydroxyalkyl carbonate. Alternatively, a functional compound containing a ketal of a 1,2-diol having the structure:

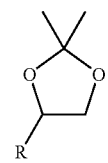

can be ring-opened with water at temperatures of at least 60° C., preferably with a trace amount of acid, to form a 1,2-glycol, which is then further reacted with diethyl carbonate to form the cyclic carbonate.

Cyclic carbonates typically have 5–6-membered rings, as is known in the art. Five-membered rings are preferred, due to their ease of synthesis and greater degree of commercial availability. Six-membered rings can be synthesized by reacting phosgene with 1,3-propane diol under conditions known in the art for the formation of cyclic carbonates. Preferred hydroxyalkyl cyclic carbonates used in the practice can be represented by the formula:

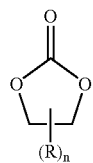

where R (or each instance of R if n is more than 1) is a hydroxyalkyl group of 1–18 carbon atoms, preferably 1–6 carbon atoms, and more preferably 1–3 carbon atoms, which may be linear or branched and may have subsituents in addition to the hydroxyl (which itself may be primary, secondary, or tertiary), and n is 1 or 2, which may be substituted by one or more other substituents such as blocked amines or unsaturated groups. More preferably, R is —$C_mH_{2m}$OH where the hydroxyl may be primary or secondary and m is 1 to 8, and even more preferably, R is —$(CH_2)_p$—OH where the hydroxyl is primary and p is 1 to 2.

Lactones that can be ring opened by an active hydrogen are well-known in the art. They include, for example, ε-caprolactone, γ-caprolactone, β-butyrolactone, β-propriolactone, γ-butyrolactone, α-methyl-γ-butyrolactone, β-methyl-γ-butyrolactone, γ-valerolactone, δ-valerolactone, γ-nonanoic lactone, γ-octanoic lactone, and pentolactone. In one preferred embodiment, the lactone is ε-caprolactone. Lactones useful in the practice of the invention can also be characterized by the formula:

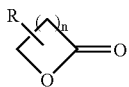

wherein n is a positive integer of 1 to 7 and R is one or more H atoms, or substituted or unsubstituted alkyl groups of 1–7 carbon atoms.

The lactone ring-opening reaction is typically conducted under elevated temperature (e.g., 80–150° C.). The reactants are usually liquids so a solvent is not necessary. However, a solvent may be useful in promoting good conditions for the reaction even if the reactants are liquid. Any non-reactive solvent may be used, including both polar and nonpolar organic solvents. Examples of useful solvents include toluene, xylene, methyl ethyl ketone, methyl isobutyl ketone, and the like. A catalyst is preferably present. Useful catalysts include proton acids (e.g., octanoic acid, Amberlyst® 15 (Rohm & Haas)), and tin catalysts (e.g., stannous octoate). Alternatively, the reaction can be initiated by forming a sodium salt of the hydroxyl group on the molecules to react with the lactone ring.

The lactone ring-opening reaction provides chain extension of the molecule if sufficient amounts of the lactone are present. The relative amounts of the carbamate or urea compound (A) and the lactone can be varied to control the degree of chain extension. The opening of the lactone ring with a hydroxyl or amine group results in the formation of an ester or amide and an OH group. The OH group can then react with another available lactone ring, thus resulting in chain extension. The reaction is thus controlled by the proportion of lactone in the relative to the amount of initiator compound (A). In the practice of the present invention, the ratio of equivalents of lactone to equivalents of active hydrogen groups on (A) is preferably from 0.1:1 to 10:1, and more preferably from 1:1 to 5:1. When the lactone is opened with with an acid, the resulting compound has an acid group, which can then be converted to a hydroxyl group by well-known techniques such as reaction with ethylene oxide.

A compound (A)(1) having a hydroxyl active hydrogen group can also be reacted with a hydroxy carboxylic acid to form the carbamate- or urea-functional compound (A). Useful hydroxy carboxylic acids include dimethylhydroxypropionic acid, hydroxy stearic acid, tartaric acid, lactic acid, 2-hydroxyethyl benzoic acid, and N-(2-hydroxyethyl)ethylene diamine triacetic acid. The reaction can be conducted under typical transesterification conditions, e.g., temperatures from room temperature to 150° C. with transesterification catalysts such as such as calcium octoate, metal hydroxides (e.g., KOH), Group I or II metals (e.g., Na, Li), metal carbonates (e.g., $K_2CO_3$) which may be enhanced by use in combination with crown ethers, metal oxides (e.g., dibutyltin oxide), metal alkoxides (e.g., $NaOCH_3$, $Al(OC_3H_7)_3$), metal esters (e.g., stannous octoate, calcium octoate, or protic acids (e.g., $H_2SO_4$), $MgCO_3$, or $Ph_4SbI$. The reaction may also be conducted at room temperature with a polymer-supported catalyst such as Amberlyst-15® (Rohm & Haas) as described by R. Anand, *Synthetic Communications*, 24(19), 2743–47 (1994), the disclosure of which is incorporated herein by reference.

In one embodiment of the invention, after the reaction of compound (A) with the lactone or hydroxy carboxylic acid is complete, the reaction product (hereinafter referred to as (A)(1) may be further reacted with a compound (A)(2) that is reactive with the hydroxyl groups on a plurality of molecules of (A)(1), but that is not reactive with the carbamate or urea groups thereon. Thus, in the final product produced by this reaction, the residue of compound (A)(2) can be described as a core to which a plurality of carbamate- or urea-functional residues of compound (A)(1) are attached. It is also contemplated that compound (A)(1) may be admixed with other compounds comprising a hydroxyl group plus a carbamate or urea group (e.g., hydroxypropyl carbamate) prior to the reaction with compound (A)(2). In such a case, the resulting reaction product mixture will reflect the stoichiometric ratio of compound (A)(1) to such other compounds.

Compounds that are useful as (A)(2) include polyisocyanates, dialkyl carbonates, cyclic carbonates, $CO_2$, phosgene, acetals, cyclic or linear phosphazene-based compounds, substituted or unsubstituted cyclic siloxanes or silanes, or substituted or unsubstituted linear siloxanes or silanes, which may be described by the formula $SiX_mR_n$ where X is a group that is reactive with protons, such as a halide, alkoxy, hydride, or acetate, R is a group that is non-reactive with protons such as alkyl, silane, or siloxane, m=2–4, and m+n=4, $SO_2$ sources such as $SO_3$ or $SO_2Cl_2$, $POCl_3$, $POCl_2R$ where R is alkyl or aryl. With certain of the compounds (A)(2), a diol may also be included in the reaction mixture comprising (A)(1) and (A)(2) to obtain chain extension with carbamate or urea termination. This can be done, for example, with phosgene where the phosgene/diol reaction results in chain extension and the reaction of phosgene with compound (A)(1) results in chain termination with a carbamate or urea group.

The polyisocyanate can be an aliphatic polyisocyanate, including a cycloaliphatic polyisocyanate or an aromatic polyisocyanate. Useful aliphatic polyisocyanates include aliphatic diisocyanates such as ethylene diisocyanate, 1,2-diisocyanatopropane, 1,3-diisocyanatopropane, 1,6-diisocyanatohexane, 1,4-butylene diisocyanate, lysine diisocyanate, 1,4-methylene bis-(cyclohexyl isocyanate) and isophorone diisocyanate. Useful aromatic diisocyanates and araliphatic diisocyanates include the various isomers of toluene diisocyanate, meta-xylylenediioscyanate and para-xylylenediisocyanate, also 4-chloro-1,3-phenylene diisocyanate, 1,5-tetrahydro-naphthalene diisocyanate, 4,4'-dibenzyl diisocyanate and 1,2,4-benzene triisocyanate can be used. In addition, the various isomers of $\alpha,\alpha,\alpha',\alpha'$-tetramethyl xylylene diisocyanate can be used. Oligomeric or polymeric polyisocyanates prepared by reaction of an excess of monomeric polyisocyanates with a polyol may be used. Also, isocyanurates such as the isocyanurate of isophorone diisocyanate or the isocyanurate of hexamethylene diisocyanate may be used. Biurets of isocyanates such as DESMODUR® N100 from Mobay may also be useful.

Dialkyl carbonates, cyclic carbonates, $CO_2$, diphenyl carbonates, or phosgene may be used as compound (A)(2) to react with and link two (A)(1) compounds via a carbonate linking group. When phosgene is used, phosgene may be added to a solution of compound (A)(1) at a molar ratio of about 1 mole phosgene to 2 moles (A)(1) (or 2 moles (A)(1) plus other hydroxy carbamate or urea compounds such as hydroxypropyl carbamate). This reaction may be conducted at temperatures of less than 7° C. or under pressure in order to maintain phosgene in it's liquid state, or alternatively, gaseous phosgene may be bubbled through the system. A salting base (e.g., NaOH) may be used to help drive the reaction. The reaction may be conducted in virtually any aprotic solvent at temperatures of $-20°$ C. to $80°$ C. and pressures of atmospheric to 40 psi.

Cyclic carbonates or dialkyl carbonates may be used as compound (A)(2) to react with compound (A)(1) by heating (e.g., 80–200° C.) the appropriate molar mixture (2 moles (A)(1) plus any other hydroxy carbamate or urea and 1 mole cyclic carbonate or dialkyl carbonate) with a transesterification catalyst such as calcium octoate. Useful dialkyl carbonates include diethyl carbonate, dimethyl carbonate, dipropyl carbonate, diphenyl carbonate, and dibutyl carbonate. Useful cyclic carbonates include propylene carbonate, glycerine carbonate, and dimethyl ethylene carbonate. Cyclic carbonates may also be formed from any unsaturated bond by reaction of the unsaturated bond with peroxide to form an oxirane ring, followed by reaction with $CO_2$ to form the cyclic carbonate. Useful catalysts include metal hydroxides (e.g., KOH), Group I or II metals (e.g., Na, Li), metal carbonates (e.g., $K_2CO_3$) which may be enhanced by use in combination with crown ethers, metal oxides (e.g., dibutyltin oxide), metal alkoxides (e.g., $NaOCH_3$, $Al(OC_3H_7)_3$), metal esters (e.g., stannous octoate, calcium octoate), or protic acids (e.g., $H_2SO_4$), $MgCO_3$, or $Ph_4SbI$. Any solvents used should be inert to transesterification. The catalysts and/or reaction conditions may need to be adjusted to minimize transesterification of the ester groups from the ring-opened lactone in compound (A)(1). $CO_2$ may also be used as compound (A)(2) under similar conditions with similar catalysts plus it may be used at pressures of 1 to 40 atm.

Compounds having inorganic reactive groups may also be used to react with the hydroxyl groups of compound (A)(1). These include phosphorus compounds such as $POCl_3$ or hexachlorocyclotriphosphazene, $SO_2$ sources such as $SO_3$ or $SO_2Cl_2$ or silane-based systems such as substituted or unsubstituted cyclic siloxanes or silanes, or substituted or unsubstituted linear siloxanes or silanes, which may be described by the formula $SiX_mR_n$ where X is a group that is reactive with protons, such as a halide, alkoxy, hydride, or acetate, R is a group that is non-reactive with protons such as alkyl, silane, or siloxane, m=2–4, and m+n=4.

Phosphazene-based compounds (e.g., hexachlorocyclotriphosphazene) or $POCl_3$ may be used as compound (A)(2) to react with (A)(1). In a typical reaction, one equivalent (based on chlorine content) of the phosphorus reagent is dissolved in a dry ether solvent such as diethyl ether of tetrahydrofuran to form a solution of approximately 50%. 1.5 equivalents of sodium hydride are added followed by one equivalent of (A)(1) (or (A)(1) plus other hydroxy carbamate or urea compounds). The mixture is allowed to exotherm to the reflux temperature of the solvent, with the reaction temperature controlled by the addition rate of the (A)(1) compound. After addition of the (A)(1) compound is complete, the reaction mixture is heated to reflux and held for 2–3 hours. The mixture is then cooled, filtered to remove sodium chloride and any unreacted sodium hydride, and the solvent removed under vacuum.

Silane-based compounds may also be used as compound (A)(2). Such compounds may be described by the formula $SiX_mR_n$ where X is a group that is reactive with protons, such as a halide, alkoxy, hydride, or acetate, R is a group that is non-reactive with protons such as alkyl, silane, or siloxane, m=2–4, and m+n=4. These compounds may react with (A)(1) in any dry aprotic solvent (e.g., tetrahydrofuran) under conditions known in the art, which may depend on the nature of the X group. When X is a hydride, the reaction is preferably begun with chilled reactants (e.g., 0° C.) under an inert atmosphere using catalysts such as tin catalysts. After the addition of materials is complete, amd dry methanol is added to react with any free remaining Si—H bonds. If X is a halide, the reaction is preferably begun under an inert atmosphere at room temperature. The mixture is then heated to reflux to drive the reaction to completion. HCl is given off as a by-product. If X is alkoxy, the reaction is preferably begun under an inert atmosphere at room temperature, which may be maintained for the duration of the reaction. A molecular sieve may be used to absorb the alcohol side product that is formed. Slightly basic or acidic pH will accelerate this reaction; however, it will also accelerate the formation of Si—O—Si bonds.

For $SO_2$ sources, the $SO_3$ can be reacted with the (A)(1) by bubbling $SO_3$ through the (A)(1) compound if it is in liquid form or by dissolving (A)(1) in a solvent and then bubbling $SO_3$ through the solution. The reaction of $SO_2Cl_2$ with (A)(1) may be assisted by the pre-reaction of (A)(1) with Na or NaOR (where R is an organic radical).

In another embodiment of the invention, after the reaction to form compound (A)(1) is complete, (A)(1) may be reacted with a component (A)(3) that is reactive with compound (A)(1) to convert a hydroxyl group on compound (A)(1) to a carbamate group, or a component comprising a group that is reactive with a hydroxyl group on compound (A)(1) and a carbamate or urea group or group that can be converted to carbamate or urea.

A number of compounds may be used as compound (A)(3) to convert a hydroxyl group on compound (A)(1) to a carbamate group. Hydroxyl groups can be converted to carbamate groups by reaction with a monoisocyanate (e.g., methyl isocyanate) to form a secondary carbamate group or with cyanic acid (which may be formed by the thermal decomposition of urea) to form a primary carbamate group (i.e., unsubstituted carbamates). This reaction is performed preferably in the presence of a catalyst as is known in the art. A hydroxyl group can also be reacted with phosgene and then ammonia to form a compound having primary carbamate group(s), or by reaction of a hydroxyl with phosgene and then a primary amine to form a compound having secondary carbamate groups.

Various compounds can be used as compound (A)(3) that have a group that is reactive with the hydroxyl group on (A)(1) and a carbamate or urea group or a group that can be converted to carbamate or urea. Alkyl carbamates (e.g., methyl carbamate, butyl carbamate) or substituted alkyl carbamates (e.g., hydroxypropyl carbamate) can be transesterified with the hydroxyl group on compound (A)(1). This reaction is performed under heat, preferably in the presence of a catalyst such as an organometallic catalyst (e.g., dibutyltin dilaurate). A methylol acrylamide can be reacted with the hydroxyl group on (A)(1) and then converted to carbamate. In this reaction, the unsaturated bond is then reacted with peroxide, $CO_2$, and ammonia as described above. The epoxy groups are then reacted with $CO_2$ to form cyclic carbonate groups, which are converted to carbamate groups by reaction with ammonia. Partially-blocked toluene diisocyanate can also be used as compound (A)(3). In one embodiment, the unblocked isocyanate on the partially-blocked toluene diisocyanate can be reacted with the hydroxyl group on (A)(1). The other isocyanate can then be unblocked and reacted with a hydroxyalkyl carbamate (e.g., hydroxypropyl carbamate) or a hydroxy urea (e.g., hydroxyethyl ethylene urea). Alternatively, the unblocked isocyanate can be reacted with a hydroxyalkyl carbamate (e.g., hydroxypropyl carbamate) or a hydroxy urea (e.g., hydroxyethyl ethylene urea), followed by unblocking of the other isocyanate group and reaction with the hydroxyl group on compound (A)(1). Other polyisocyanates can be used to append carbamate or urea groups onto the hydroxyl group on (A)(1), but they will result in competing side reactions where the polyisocyanate reacts with more than one (A)(1) molecule or more than one hydroxyalkyl carbamate or hydroxy urea.

Carbamate- or urea-functional compounds prepared according to the present invention may be used in curable compositions such as curable coating compositions, and cured by reaction with a component (B) that is a compound having a plurality of functional groups that are reactive with the carbamate or urea groups. Such reactive groups include active methylol or methylalkoxy groups on aminoplast crosslinking agents or on other compounds such as phenol/formaldehyde adducts, siloxane or silane groups, and anhydride groups. Examples of (B) compounds include melamine formaldehyde resin (including monomeric or polymeric melamine resin and partially or fully alkylated melamine resin), urea resins (e.g., methylol ureas such as urea formaldehyde resin, alkoxy ureas such as butylated urea formaldehyde resin), N-methylol acrylamide emulsions, isobutoxy methyl acrylamide emulsions, polyanhydrides (e.g., polysuccinic anhydride), and siloxanes or silanes (e.g., dimethyldimethoxy silane). Aminoplast resin such as melamine formaldehyde resin or urea formaldehyde resin are especially preferred. Also preferred are aminoplast resins where one or more of the amino nitrogens is substituted with a carbamate group for use in a process with a curing temperature below 150° C., as described in U.S. Pat. No. 5,300,328.

Other aspects regarding the use in curable coating compositions of compounds prepared according to the invention are described in copending U.S. patent application entitled "Curable Coating Composition", filed on even date herewith in the names of Brian Bammel, John McGee, Walter Ohrbom, Todd Seaver, Paul Harris, and John Rehfuss, the disclosure of which is incorporated herein by reference.

The invention is further described in the following examples.

Preparation 1

A clean 5-liter three-necked round bottomed flask was equipped with an agitator, condenser, thermocouple, and nitrogen line. To this apparatus was added 1735.0 g ε-caprolactone, 761.9 g hydroxypropyl carbamate, 234 g xylene, and 4.4 g stannous octoate. The mixtured was stirred under nitrogen atmosphere and heated to a temperature of 130° C. Temperature was maintained for a period of 6 hours to complete the synthesis, and then cooled.

EXAMPLE 1

Coating Composition

A clearcoat composition was prepared by mixing 1000 g of Preparation 1, 337.4 g monomeric fully metholated melamine, and 6.1 g dodecylbenzyl sulfonic acid.

This composition was spray-applied to a variety of substrates using a conventional air atomization siphon gun. Both rigid and flexible substrates were coated. A portion of the panels were applied wet on wet over conventional high solids basecoat. For these systems, the basecoat (an industry standard high-solids OH acrylic/melamine system) was applied, followed by a 10-minute ambient flash, at which point the above-described coating composition was applied. After an additional 5 minutes ambient flash, the panels were baked at 250° F. for 30 minutes.

The coating composition of the Example resulted in a contiguous cured hard clear film. The measured VOC of the clearcoat mixture was found to be 1.2 lbs/gal.

Preparation 2

A clean 12-liter three-necked round bottomed flask was equipped with an agitator, condenser, thermocouple, and nitrogen line. To this apparatus were added 6033 g ε-caprolactone, 2516 g hydroxypropyl carbamate, 450 g toluene, and 15 g stannous octoate. The mixtured was stirred under nitrogen atmosphere and heated to a temperature of 130° C. Temperature was maintained for Preparation 3

2092 g of the component prepared according to Preparation 2, 412 g 1,6-hexamethylene diisocyanate was added under nitrogen atmosphere to a 5-liter three-necked round bottomed flask was equipped with an agitator, condenser, thermocouple, and nitrogen line. The mixture was slowly heated to 60° C. at which point the mixture exothermed. The mixture was cooled such that a maximum exotherm temperature of 99° C. was reached, after which a batch temperature of 86° C. was maintained for a period of 4.25 hours. The mixture was cooled and diluted with 286.7 g n-butyl acetate.

EXAMPLE 2

A clearcoat was prepared by mixing 166 g of the material prepared according to Preparation 3, 33.7 g monomeric fully methylated melamine, 5.22 g of a solution of blocked dodecylbenzyl sulfonic acid (25% active), 5.22 g Tinuvin® 1130, 0.87 g polyacrylate additive solution, 1.45 g surface modifier additive solution, 4.25 g n-butyl acetate and 42.5 g ethylene glycol butyl ether acetate.

The coating composition was spray-applied to a variety of substrates using a conventional air atomization siphon gun. Both rigid and flexible substrates were coated. A portion of the panels were applied wet on wet over conventional high solids basecoat. For these systems, the basecoat (an industry standard high-solids OH acrylic/melamine system) was applied, followed by a 10 minute 200° F. flash. After cooling, the coating mixture was applied directly to the basecoat. After an additional 15 minutes ambient flash, the panels were baked at 250° F. for 30 minutes.

The coating composition of the Example resulted in a contiguous cured hard clear film. The measured VOC of the clearcoat mixture was found to be 3.07 lbs/gal.

Preparation 4

A three-necked 1-liter flask was equipped with an agitator, thermocouple, nitrogen line, and condenser. To the flask were added 59.5 parts Hydroxypropyl carbamate, 171.2 parts ε-caprolactone, 98.8 parts xylene, and 0.4 parts stannous octoate under nitrogen atmosphere. The mixture was heated to 130° C. for a period of 10 hours, at which point 0.2 parts additional stannous octoate were added. The mixture was heated to 145° C. for a period of 1 hour and cooled.

Preparation 5

A three-necked 1-liter flask was equipped with agitator in the center neck, a thermocouple and nitrogen line in one neck and a trap in the third to condense and collect volatiles with a mixture of dry ice and isopropanol.

125.0 parts of Preparation 4, 11.2 parts diethyl carbonate, and 4.0 parts dibutyltin dimethoxide were added to the flask under nitrogen atmosphere. Heat was applied such that temperature was maintained around 100° C. for three hours during which time volatiles were collected in the trap. Recovered ethanol as well as diethyl carbonate distilled to trap were monitored by gas chromatograph. Periodically, additions of diethyl carbonate were made to the flask to replenish loss to the trap. The mixture was heated for an additional period of 10.5 hours at temperatures ranging from 90–132° C. with continued monitoring of recovered ethanol and replenishment of diethyl carbonate as needed.

The resulting resin was reduced with 29.8 parts amyl acetate.

EXAMPLE 3

A clearcoat was prepared by combining 10 parts Preparation 5, 2 parts Resimene® 747, 1.8 parts Solvesso® Aromatic 100 solvent mixture, and 0.48 parts docecylbenzylsulfonic acid. Once homogenious, the mixture was drawn over a glass plate, and cured at 250° F. for 30 minutes. The result was a tough, flexible, solvent-resistant coating.

Preparation 6

In a three necked three liter flask equipped with an agitator, thermocouple, nitrogen line, and condenser, were added 841.5 g hydroxypropyl carbamate, 806.9 g ε-caprolactone, and 2.8 g stannous octoate under nitrgen atmosphere. The mixture was heated to a temperature of 130° C. for a period of 5.5 hours and then cooled to room temperature.

Preparation 7

To 200 parts of Preparation 6 was added 102.7 parts of urea, and 1.6 parts of diethylene triamine. The system was heated to 130° C. and held for 1 hour. The system was then heated to 140° C. for 5.5 hours. This resulted in the formation of cyanic acid from the thermal decomposition of the urea, which reacted with the hydroxyl groups on the Preparation 1 compound form carbamate groups. The resulting solid product was washed with ethyl acetate, disolved in methylene chloride, and filtered. The methylene chloride was then removed by evaporation to yield the final product.

EXAMPLE 4

The following components were mixed and drawn down on glass substrate to form an 8 mm-thick layer:

| | |
|---|---|
| 6.2 g | Preparation 7 |
| 1.7 g | Resimene ® 747 melamine resin |
| 0.04 g | dodecylbenzene sulfonic acid |
| 10 g | amyl acetate |

The coated glass substrate was baked at 250° F. for 30 minutes, resulting in a clear tack-free film that passed 200 methylethyl ketone double rubs with only surface scratches.

The invention has been described in detail with reference to preferred embodiments thereof. It should be understood, however, that variations and modifications can be made within the spirit and scope of the invention.

What is claimed is:

1. A coating composition comprising a carbamate- or urea-functional ester-containing compound, said compound comprising the reaction product of a lactone or hydroxy carboxylic acid with a second compound comprising a carbamate or urea group or a group that can be converted to a carbamate or urea group, and an active hydrogen group capable of reacting with the hydroxycarboxylic acid or in a ring-opening reaction with a lactone.

2. A coating according to claim 1 wherein said active hydrogen group on said second compound is a hydroxyl group.

3. A coating according to claim 1 wherein said active hydrogen group on said second compound is an amino group.

4. A coating composition according to claim 1 wherein said second compound is a β-hydroxy carbamate that is a product of a ring-opened cyclic carbonate.

* * * * *